United States Patent
Niu et al.

(10) Patent No.: US 10,799,587 B2
(45) Date of Patent: *Oct. 13, 2020

(54) ION IMPLANTATION OF NEUTRON CAPTURE ELEMENTS INTO NANODIAMOND PARTICLES TO FORM COMPOSITION FOR NEUTRON CAPTURE THERAPY USAGE

(71) Applicants: Huan Niu, Taipei (TW); Chien Hsu Chen, Hsinchu (TW); Causon Ko-Chuan Jen, San Jose, CA (US)

(72) Inventors: Huan Niu, Taipei (TW); Chien Hsu Chen, Hsinchu (TW); Causon Ko-Chuan Jen, San Jose, CA (US)

( * ) Notice: Subject to any disclaimer, the term of this patent is extended or adjusted under 35 U.S.C. 154(b) by 620 days.

This patent is subject to a terminal disclaimer.

(21) Appl. No.: 15/151,510

(22) Filed: May 11, 2016

(65) Prior Publication Data

US 2017/0326236 A1    Nov. 16, 2017

(51) Int. Cl.
  *A61K 41/00* (2020.01)
  *A61K 47/69* (2017.01)
  *A61K 31/704* (2006.01)

(52) U.S. Cl.
  CPC ........ *A61K 41/0095* (2013.01); *A61K 31/704* (2013.01); *A61K 41/009* (2013.01); *A61K 47/6929* (2017.08)

(58) Field of Classification Search
  None
  See application file for complete search history.

(56) References Cited

U.S. PATENT DOCUMENTS 6,107,102 A * 8/2000 Ferrari ............... A61K 9/127
                                                      424/417
6,458,430 B1 * 10/2002 Bernstein ............ C23C 14/042
                                                      257/E21.143

FOREIGN PATENT DOCUMENTS

| CN | 101154476 A | 4/2008 |
| CN | 101879427 A | 11/2010 |
| RU | 20130115568 A | 10/2014 |

OTHER PUBLICATIONS

Zhao, L., et al., "Polyglycerol-coated nanodiamond as a macrophage-evading platform for selective drug delivery in cancer cells", Biomaterials, 2014, pp. 5393-5406 (Year: 2014).*
Hwang, K.C., et al., "Neutron capture nuclei-containing carbon nanoparticles for destruction of cancer cells", Biomaterials, 2010, pp. 8419-8425 (Year: 2010).*
Zeidler, J.R., et al., "Carrier activation and mobility of boron-dopant atoms in ion-implanted diamond as a function of implantation conditions", Phys. Rev. B., 1993, pp. 2065-2071 (Year: 1993).*
Lu, Y., et al., "Boron-rich inclusions and boron distribution inHPHT polycrystalline superconducting diamond", Carbon 86, pp. 156-162 (Year: 2015).*
Ekimov, E., et al., "Structure and superconductivityof isotope-enriched boron-doped diamond" Sci. Tecnol. Adv. Mater., pp. 1-6 (Year: 2008).*
Garrett, D.J., et al., "In vivobiocompatibility of boron doped and nitrogen includedconductive-diamond for use in medical implants", J. Biomedical Mater. Res., pp. 19-26. (Year: 2016).*

* cited by examiner

*Primary Examiner* — Michael G. Hartley
*Assistant Examiner* — Lance W Rider
(74) *Attorney, Agent, or Firm* — Mark M. Friedman

(57) ABSTRACT

A composition for neutron capture therapy and a method of preparing the same are provided. The composition includes at least one nanodiamond particle and at least one neutron capture element, in which the at least one neutron capture element is embedded into the at least one nanodiamond particle by using an ion implantation system.

14 Claims, 8 Drawing Sheets

ION IMPLANTATION OF NEUTRON CAPTURE ELEMENTS INTO NANODIAMOND PARTICLES TO FORM COMPOSITION FOR NEUTRON CAPTURE THERAPY USAGE

FIELD OF THE INVENTION

The present invention relates to a composition for neutron capture therapy (NCT) and a method of preparing the same, and more particularly to an ion implantation of neutron capture elements into nanodiamond particles to form a composition for neutron capture therapy usage.

BACKGROUND OF THE INVENTION

Neutron capture therapy is a cancer therapy which utilizes radiation emitted as a result of the neutron-capture reaction with neutron capture elements, such as boron-10, gadolinium-157, etc., located in tumor cells and thermal neutrons irradiated from the outside of the body. Specifically, in NCT, a patient is firstly administered a tumor localizing drug having neutron capture elements which have a high neutron capture cross section to capture neutrons. After the tumor localizing drug is introduced to tumor cells, the patient is radiated with epithermal neutrons to destroy most of tumor cells. For example, please refer to FIG. 1, which depicts a schematic diagram of boron neutron capture therapy (BNCT) reaction. In BNCT, compounds containing the stable isotope $^{10}B$ particle 110 are introduced into tumor cells, and then are irradiated with thermal neutrons 100. Due to the $^{10}B$ particle 110 having a high neutron capture cross section, the $^{10}B$ particle 110 will capture the neutron 100, and an unstable isotope $^{11}B^*$ particle 120 is thus formed. The $^{11}B^*$ particle 120 will decay into an energetic alpha particle 130 and a recoiling $^{7}Li$ nuclei 140 to destroy tumor cells nearby. Unfortunately, success of BNCT is very limited, because of the fact that the amount of $^{10}B$ containing drug being effectively delivered into tumor cells doesn't reach a desired dosage. For example, BPA and BSH drugs are mostly employed in BNCT for brain tumors, but the progress is very limited so that new drugs are still being developed and proposed. Thus, there are several generations of neutron capture elements containing drugs have been developed to improve the neutron capture elements uptake ratio on tumor cells.

On the other hand, with the development of nanotechnology, nanomedicine for general biomedical applications in cancer diagnosis and treatment is one of the areas that has many activities ongoing and has yielded some positive results in recent years. In the biomedical field, scientists have reported the use of magnetic nanoparticles for glioblastoma (brain tumor) patient's treatment through thermotherapy. Also, scientists find that gold nano-shells inside tumor cells can absorb light and convert photon energy to heat up and suppress tumor cells growth in mice. Moreover, it is understood that nanoparticles provide a promising platform to conjugate with conventional cancer treatment drugs for non-invasive, and directly target to tumor cells for diagnosis and treatment with less toxicity and less damage to the immune system and normal tissues. Therefore, scientists have been devoting themselves to the synthetization of nanoparticles with drug delivery agent through modifying nanoparticles' surface functional properties to form various "tumor targeting drugs", where the drug delivery agent contains neutron capture elements for specific cancer NCT.

However, in the above-mentioned conventional NCT, the neutron capture elements containing composition is additionally coupled on a surface of the nanoparticle, so that the amount of the neutron capture elements carrying on each nanoparticle is limited. That is, the difficulty is to deliver high concentration of neutron capture elements into the tumor cells while keeping the concentration of the neutron capture elements relatively low in the surrounding normal cells whereby thermal neutron irradiation can destroy most of tumor cells but not damage the nearby normal cells. Furthermore, there are many different types of nanomaterials in different forms being used for different purposes, e.g. carbon nanotube, graphene, nanocomposites, nanofibers, nanowires, and others organic compound particles, but some nanoparticles have several disadvantages including cytotoxicity and poor biocompatible properties.

Accordingly, it is necessary to provide a composition for treating tumor cells and method of preparing the same to solve the technical problems in the prior art.

SUMMARY OF THE INVENTION

In order to solve the above-mentioned technical problems, an objective of the present invention is to provide a composition and a method of preparing the same, in which the composition comprises neutron capture elements having a high neutron capture cross section embedded into a nanodiamond particle by using an ion implantation technique for treating tumor cells through NCT. Furthermore, the composition is prepared by synthesizing with a targeting drug agent and to deliver such a nanodiamond therapeutic agent to tumor cells for NCT. Hence, in comparison to conventional NCT drug delivery systems, the uptake of neutron capture elements containing compositions by the tumor cells according to the present invention can be significantly increased, thereby enhancing the NCT effect.

In order to achieve the above objective, the present invention provides a composition for neutron capture therapy, comprising: at least one nanodiamond particle and at least one neutron capture element, wherein the at least one neutron capture element is embedded into the at least one nanodiamond particle by using an ion implantation system.

In one preferred embodiment of the present invention, the at least one neutron capture element comprises boron-10 or gadolinium-157.

In one preferred embodiment of the present invention, the ion implantation system comprises: an ion source assembly, for generating ions; an extraction assembly, for extracting the ions from the ion source assembly to form an ion beam; an analyzing magnet, for selecting the at least one neutron capture element from the ion beam; and an end station, for supporting a workpiece which holds the at least one nanodiamond particle and located in a path of the ion beam such that the at least one neutron capture element is implanted into the workpiece thereby to embed the at least one neutron capture element into the at least one nanodiamond particle.

In one preferred embodiment of the present invention, the ion implantation system comprises a plasma immersion ion implantation.

In one preferred embodiment of the present invention, the composition further comprises at least one chemotherapeutic drug, wherein the at least one chemotherapeutic drug is conjugated with the at least one nanodiamond particle embedded with the at least one neutron capture element.

In one preferred embodiment of the present invention, the at least one chemotherapeutic drug is selected from the group consisting of doxorubicin and daunorubicin.

In one preferred embodiment of the present invention, the composition further comprises at least one neutron capture therapy drug coupled with the at least one nanodiamond particle embedded with the at least one neutron capture element for targeted delivery of the composition to tumor cells.

In one preferred embodiment of the present invention, the at least one neutron capture therapy drug is selected from the group consisting of BPA, BSH, and BSH-3R.

In one preferred embodiment of the present invention, the composition further comprises at least one drug delivery agent connected with the at least one nanodiamond particle embedded with the at least one neutron capture element to deliver the at least one nanodiamond particle embedded with the at least one neutron capture element to tumor cells for performing neutron capture therapy.

Another object of the present invention is to provide a method of preparing a composition for neutron capture therapy, comprising providing a workpiece which holds at least one nanodiamond particle; disposing the workpiece on an ion implantation system; and embedding at least one neutron capture element into the at least one nanodiamond particle by using the ion implantation system.

In one preferred embodiment of the present invention, the step of embedding at least one neutron capture element into the at least one nanodiamond particle by using the ion implantation system comprises: generating ions by an ion source assembly of the ion implantation system; extracting the ions from the ion source assembly to form an ion beam by an extraction assembly of the ion implantation system; selecting the at least one neutron capture element from the ion beam by an analyzing magnet of the ion implantation system; and implanting the at least one neutron capture element into the workpiece so as to embed the at least one neutron capture element into the at least one nanodiamond particle.

In one preferred embodiment of the present invention, the workpiece is disposed and supported by an end station of the ion implantation system, and the end station is located at a path of the ion beam.

In one preferred embodiment of the present invention, the method of preparing a composition further comprises: conjugating at least one chemotherapeutic drug with the at least one nanodiamond particle embedded with the at least one neutron capture element. Preferably, the at least one chemotherapeutic drug is selected from the group consisting of doxorubicin and daunorubicin.

In one preferred embodiment of the present invention, the method of preparing a composition further comprises: coupling at least one neutron capture therapy drug to the at least one nanodiamond particle embedded with the at least one neutron capture element for targeted delivery of the composition to tumor cells. Preferably, the at least one neutron capture therapy drug is selected from the group consisting of BPA, BSH, and BSH-3R.

In one preferred embodiment of the present invention, the method of preparing a composition further comprises: connecting at least one drug delivery agent with the at least one nanodiamond particle embedded with the at least one neutron capture element to deliver the at least one nanodiamond particle embedded with the at least one neutron capture element to tumor cells for performing neutron capture therapy.

Another object of the present invention is to provide a method of performing neutron capture therapy in a subject, comprising administering a composition comprising at least one nanodiamond particle and at least one neutron capture element to the subject, in which the at least one neutron capture element is embedded into the at least one nanodiamond particle by using an ion implantation system.

The present invention also provides a composition for neutron capture therapy, comprising: at least one nanodiamond particle; at least one neutron capture element, wherein the at least one neutron capture element is embedded into the at least one nanodiamond particle; agent for facilitating the treatment of tumor cells being connected with the nanodiamond particle embedded with the at least one neutron capture element.

In one preferred embodiment of the present invention, the agent is chemotherapeutic drug. Preferably, the chemotherapeutic drug is selected from the group consisting of doxorubicin and daunorubicin.

In one preferred embodiment of the present invention, the agent is neutron capture therapy drug for targeted delivery of the composition to the tumor cells. Preferably, the neutron capture therapy drug is selected from the group consisting of BPA, BSH, and BSH-3R.

In one preferred embodiment of the present invention, the agent is a drug delivery an agent to deliver the at least one nanodiamond particle embedded with the at least one neutron capture element to the tumor cells for performing neutron capture therapy.

BRIEF DESCRIPTION OF THE DRAWINGS

In order to illustrate the technical solutions in the embodiments of the present invention or in the prior art more clearly, the following briefly introduces the accompanying drawings required for describing the embodiments or the prior art. The accompanying drawings in the following description are merely some embodiments of the present invention, and persons of ordinary skill in the art may still derive other drawings from these accompanying drawings without creative effort.

DETAILED DESCRIPTION OF THE INVENTION

Figure 1:
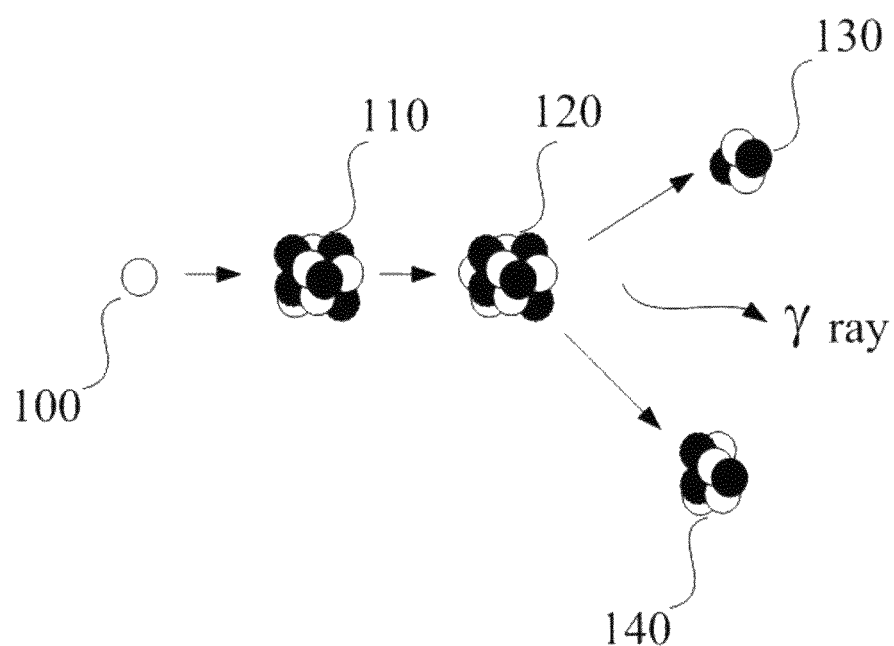
FIG. 1 depicts a schematic diagram of a boron neutron capture therapy reaction in accordance with the prior art.

Please refer to the accompanying drawings, similar parts are denoted with the same reference numerals. The following description is based on the particular embodiments of the present invention, and they should not be construed as limiting the invention to the other embodiments which are not discussed in detail herein.

Figure 2A:
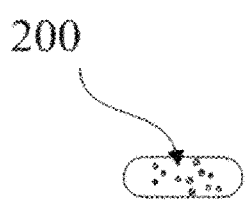
FIG. 2A shows a schematic diagram of a composition according to a first preferred embodiment of the present invention.
Figure 2B:
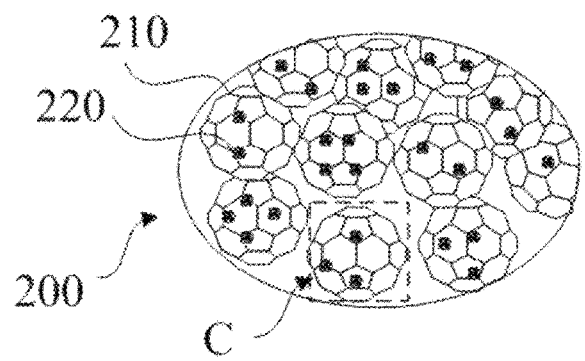
FIG. 2B shows an enlarged view of a portion of FIG. 2A.
Figure 2C:
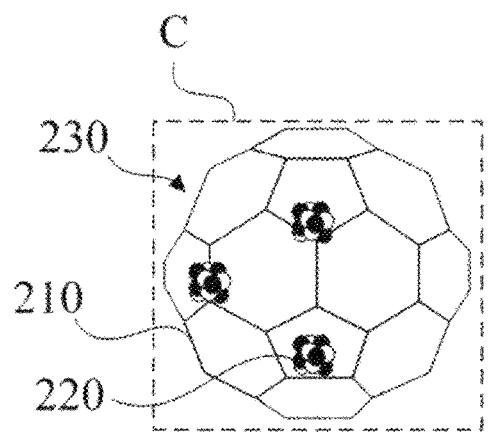
FIG. 2C shows an enlarged view of a portion C of FIG. 2B.
Figure 2D:
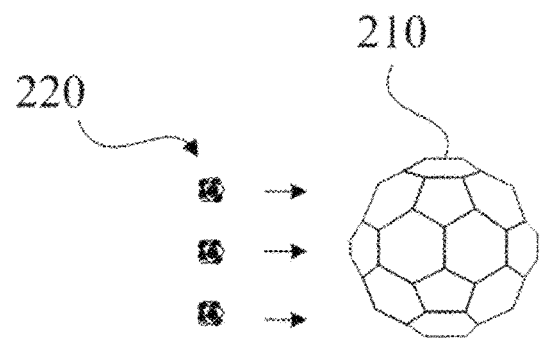
FIG. 2D is a schematic diagram showing neutron capture elements implanted into a nanodiamond particle for obtaining the composition of FIG. 2A.

Please refer to FIG. 2A, which shows a schematic diagram of a composition 200 according to a first preferred embodiment of the present invention. FIG. 2B shows an enlarged view of a portion of the composition 200 and FIG. 2C further shows an enlarged view of a portion C of FIG. 2B. As shown on FIG. 2B, the composition 200 comprises a plurality of nanodiamond particles 210 and a plurality of neutron capture elements 220. Moreover, as shown on FIG. 2C and also referring to FIG. 2D, the neutron capture elements 220 are directly implanted into each nanodiamond particle 210 by using an ion implantation system, so that each of the nanodiamond particles 210 embedded with the neutron capture elements 220 is thus formed. In FIGS. 2B and 2C, a reference numeral 230 is used to designate "the nanodiamond particle embedded with the neutron capture elements", and the composition 200 comprises a plurality of the nanodiamond particles embedded with the neutron capture elements 230. In the present invention, since the nanodiamond particles 210 exhibits no cytotoxicity to human cells, and does not induce significant abnormality in cellular functions, the nanodiamond particles 210 are of particular benefit in biomedical and medical applications, e.g. drug delivery, therapy, and diagnostic techniques. It should be noted that, the scope of the present invention is not limited to the nanodiamond particle only; any other nanoparticles which exhibit no obvious toxicity and has excellent biocompatibility for cancer diagnosis and therapies as well can be selected.

The neutron capture elements 220 are selected from atoms having a high neutron capture cross section to capture neutrons, such as boron-10, gadolinium-157, etc., so the composition 200 is suitable for use in NCT, where the nanodiamond particles 210 serve as a carrier for in vivo delivery of the neutron capture elements 220. Be it known that malignant brain tumor, glioblastoma multiforme (GBM) is a difficult tumor to treat and cure. The median survival time is less than 15 months after various therapies including surgical tumor resection, radiotherapy, and chemotherapy. Therefore, the present invention provides a new method of performing NCT in a subject including human being.

Figure 3:
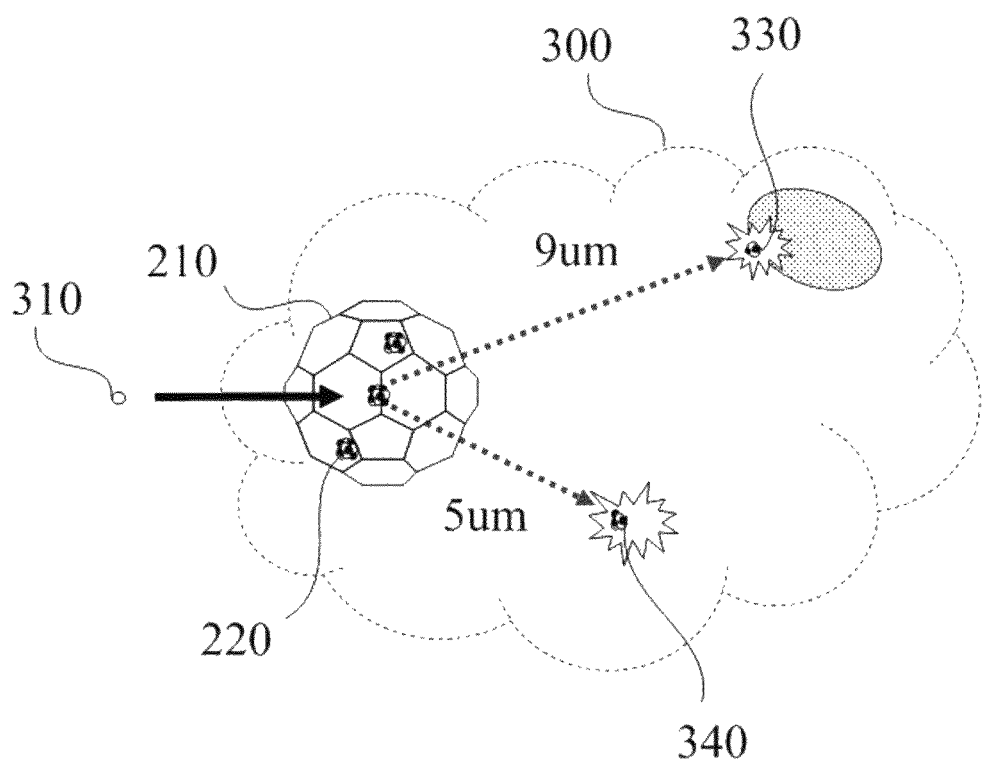
FIG. 3 shows a schematic diagram of a neutron capture therapy reaction by administering the composition of FIG. 2.

Please refer FIG. 3, which shows a schematic diagram of a neutron capture therapy reaction by administering the composition 200 of FIG. 2. The composition 200 is prepared by embedding the neutron capture elements 220, here for example $^{10}B$, into the nanodiamond particles 210, and then is further synthesized with targeting drug agent so as to deliver the nanodiamond particles 210 embedded with the neutron capture elements 220 to tumor cells. In NCT, firstly, the composition 200 is administered to the subject, and the nanodiamond particles 210 embedded with the neutron capture elements 220 will be introduced close to or within the tumor cell 300. Once the neutron capture elements 220, here for example $^{10}B$, embedded in the nanodiamond particles 210 absorbs an incoming neutron 310, $^{10}B$ 220 is then excited to an unstable $^{11}B*$, which will decay to release an alpha particle 330 and a recoiling $^{7}Li$ nuclei 340, of high linear energy transfer (LET). These high energy alpha particles 330 and recoiling $^{7}Li$ nuclei 340 have large travel ranges greater than the dimension of each nanodiamond particle 210, so they can exit from the nanodiamond particle 210 to destroy the nearby tumor cell 300. With the nanodiamond particles 210 containing the embedded neutron capture elements 220 through ion implantation, and further synthesizing to form a therapeutic agent target for NCT, the present invention can enhance the total neutron capture events for an effective treatment than before and improve the survival rate or cure rate.

Furthermore, since the nanodiamond particles 210 has a large loading capacity for synthetizing with various types of compounds/drugs due to its large surface area to volume ratio, it is advantageous to modify and utilize nanodiamond surface functional properties to conjugate with therapeutic agents for a specific purpose or multiple purposes usage, such as to deliver a drug with localized distribution to tumor cells, limited diffusion to increase uptakes in tumor cells, image capability to locate tumor cells precisely, and increased drug retention period for tumor treatment. Moreover, the nanodiamond particles 210 embedded with the neutron capture elements 220 also can be synthetized with a fluorescent agent and/or ferrocene particles for labeling and tracking tumor cells. In addition, the surface of the nanodiamond particles 210 embedded with the neutron capture elements 220 can be modified to form bonds with folate moieties to effectively target tumor cell which usually is over-expressed with folate receptors than normal cell. So that the tumor cells targeted by the nanodiamond particles 210 containing the embedded neutron capture element 220 bonded with folate moieties can have high death rate after thermal neutron irradiation.

Figure 4:
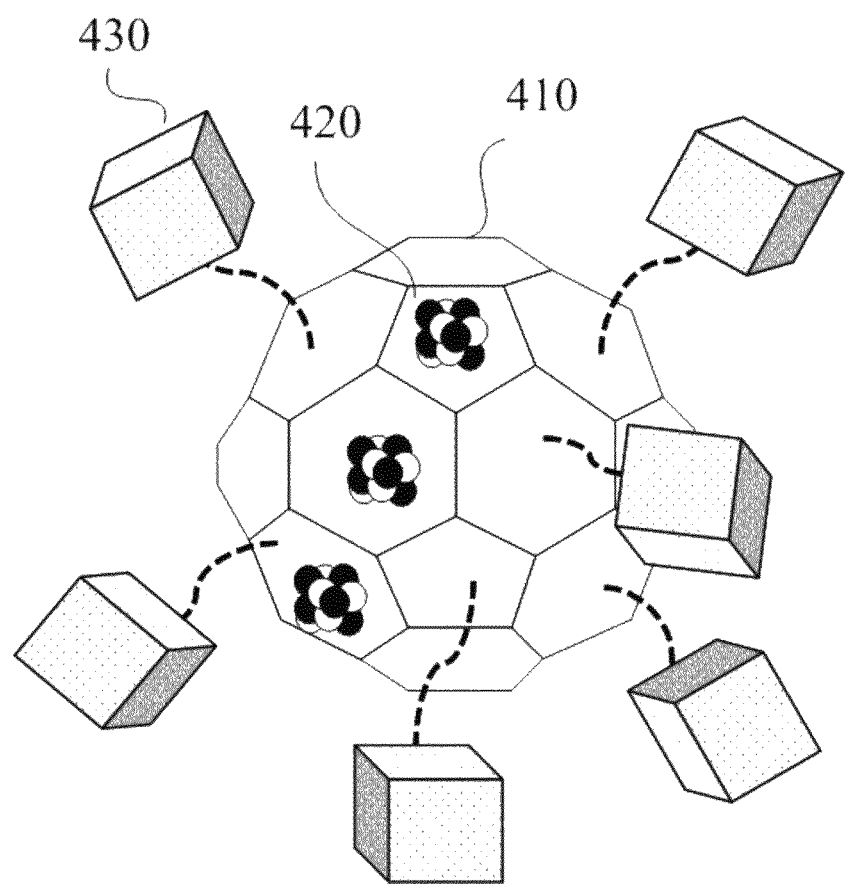
FIG. 4 shows a schematic diagram of a composition according to a second preferred embodiment of the present invention.

Please refer to FIG. 4, which shows a schematic diagram of a composition according to a second preferred embodiment of the present invention, in which each nanodiamond particle 410 not only includes a plurality of neutron capture elements 420 embedded therein, but is also conjugated with a plurality of chemotherapeutic drugs 430. The chemotherapeutic drugs 430 may be selected from one or more of doxorubicin (DOX, $(C_{27}H_{29}NO_{11})$) or daunorubicin, for addition NCT effect through neutron irradiation to enhance tumor cell suppression and destruction in various tumors with minimized required uptakes chemotherapeutic drug dose and less damage or side effects of normal tissue. It is proved that nanodiamond conjugated doxorubicin compounds have much better efficacy compared to doxorubicin alone in drug resistant cancer. Hence, due to the additional neutron capture therapy effect, this allows doctors to reduce chemotherapy dosage for patients for less side effect than from traditional chemotherapy treatments.

Figure 5:
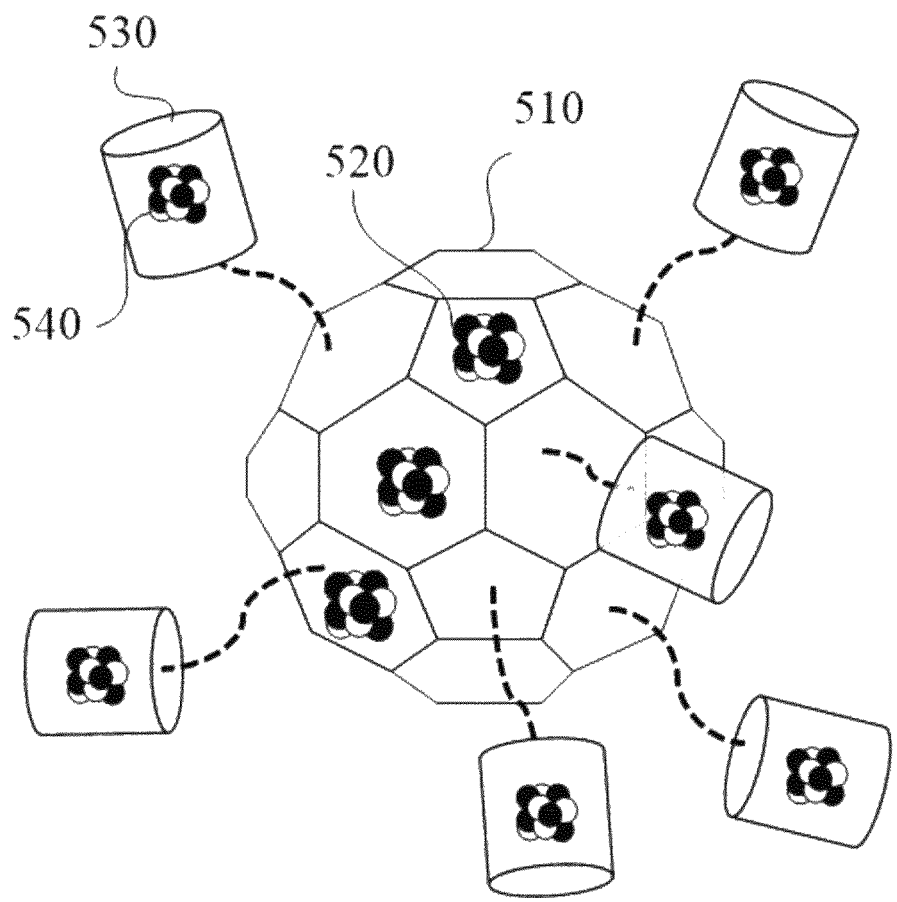
FIG. 5 shows a schematic diagram of a composition according to a third preferred embodiment of the present invention.

Please refer to FIG. 5, which shows a schematic diagram of a composition according to a third preferred embodiment of the present invention, in which each nanodiamond particle 510 not only includes a plurality of neutron capture elements 520 embedded therein, but is also coupled with a plurality of neutron capture therapy drugs 530. The neutron capture therapy drugs 530 may be selected from one or more of BPA ($C_9H_{12}BNO_4$), BSH, or BSH-3R., for tumor targeting delivery usage to increase the total neutron capture reactions near the tumor cells while minimizing the required uptake drug dose to reduce damage or side effects to normal tissue. Since the combination of the neutron capture elements 520 embedded in the nanodiamond particle 510 and the additional neutron capture elements 540, contained in the neutron capture therapy drugs 530 synthesized and attached to the surface of the nanodiamond particle 510 allows the composition to provide extra neutron capture therapy enhancement. It should be noted that the neutron capture elements 520 in the nanodiamond 510 can be a different kind of element or same kind of element to the neutron capture element 540 contained in the neutron capture therapy drugs 530. In this preferred embodiment, the total uptake of neutron capture element concentration is increased when compared to traditional neutron capture therapy drug delivery system and therefore enhances the neutron capture therapy effect.

Figure 6:
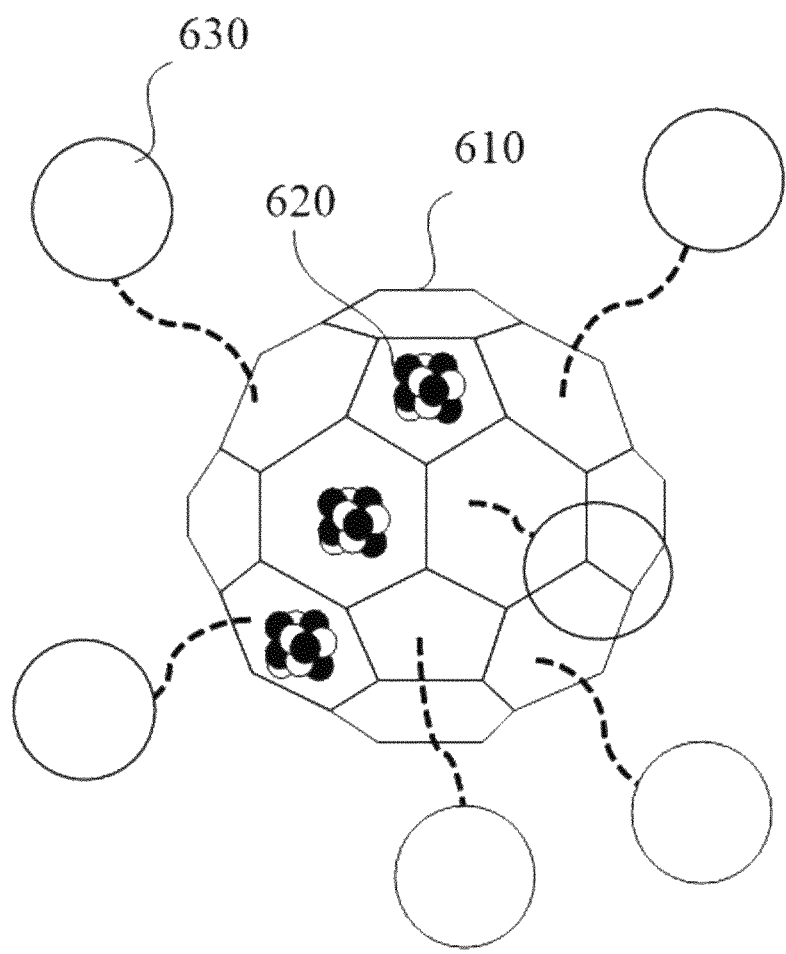
FIG. 6 shows a schematic diagram of a composition according to a fourth preferred embodiment of the present invention.

Please refer to FIG. 6, which shows a schematic diagram of a composition according to a fourth preferred embodiment of the present invention, in which each nanodiamond particle 610 not only includes a plurality of neutron capture elements 620 embedded therein, but is also connected with a plurality of specific drug delivery agents 630 to deliver the nanodiamond particle 610 which contains the neutron capture elements 620 to specific tumor cells for neutron capture therapy only, thereby allowing the development of more tumor targeting delivery drugs/agents for neutron capture therapy.

Accordingly, the present invention discloses that the neutron capture elements embedded into the nanodiamond particles by ion implantation can be used for NCT or provide additional neutron capture therapy to destroy tumor cell more effectively. The nanodiamond particles, contain the neutron capture elements through ion implantation, can be prepared and form compositions to be delivered to specific tumor cells with a high uptake concentration at tumor cells. The high concentration of the nanodiamond particles which contain neutron capture elements at the tumor cells can destroy tumor cells via neutron irradiation.

Figure 7:
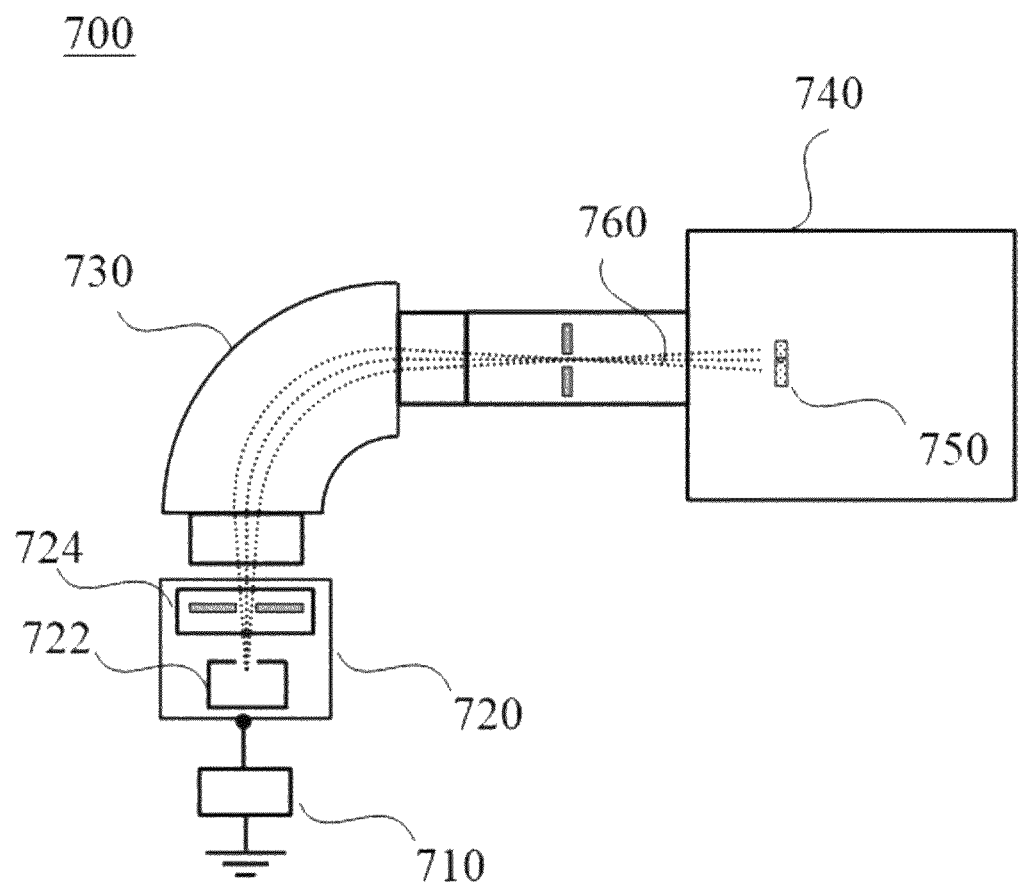
FIG. 7 depicts a schematic diagram showing a method of preparing a composition by using an ion implantation system.

Please refer to FIG. 7, which depicts a schematic diagram showing a method of preparing a composition by using an ion implantation system 700. The ion implantation system 700 comprises a high voltage power supply 710, an ion source assembly 720, an arc chamber 722, an extraction assembly 724, an analyzing magnet 730, and an end station 740. The method of preparing the composition according to the present invention comprises the steps of: providing a workpiece 750 which holds nanodiamond particles; disposing the workpiece 750 at the end station 740 of the ion implantation system 700; generating ions by the ion source assembly 720 from feed materials into the arc chamber 722; extracting the ions from the ion source assembly 720 to form an ion beam 760 by the extraction assembly 724 which provides electrical potential difference between the ion source assembly 720 and the extraction assembly 724, so that the ion beam 760 gains energy to leave the ion source assembly 720 toward downstream; selecting desired neutron capture elements from the ion beam 760 by the analyzing magnet 730; and implanting the workpiece 750 by the ion beam 760 with a controlled final energy to embed the neutron capture elements into the nanodiamond particles, where the workpiece 750 is located in a path of the ion beam 760.

In this embodiment, the neutron capture element, $^{10}B$ as an example, can be introduced through feeding the feed material of $BF_3$ gas to the ion source assembly 720 of the ion implantation system 700. Inside the ion source assembly 720, many different ionized electrical charge particles can be formed, e.g. $^{10}B^+$ $^{11}B^+$, $BF^+$, $BF_2^+$ . . . etc. Once they obtain energy through the extraction system 724 and enter the analyzing magnet 730, only $^{10}B^+$ will be selected through the analyzing magnet 730 by setting and separated from other undesired ions through different bending radius. This ion beam 760 including $^{10}B^+$ particles enter the end station 740 and bombard the workpiece 750, which holds nanodiamond particles. The $^{10}B^+$ particles embedded into the nanodiamond particles can be used to prepare a composition for neutron capture therapy.

Figure 8:
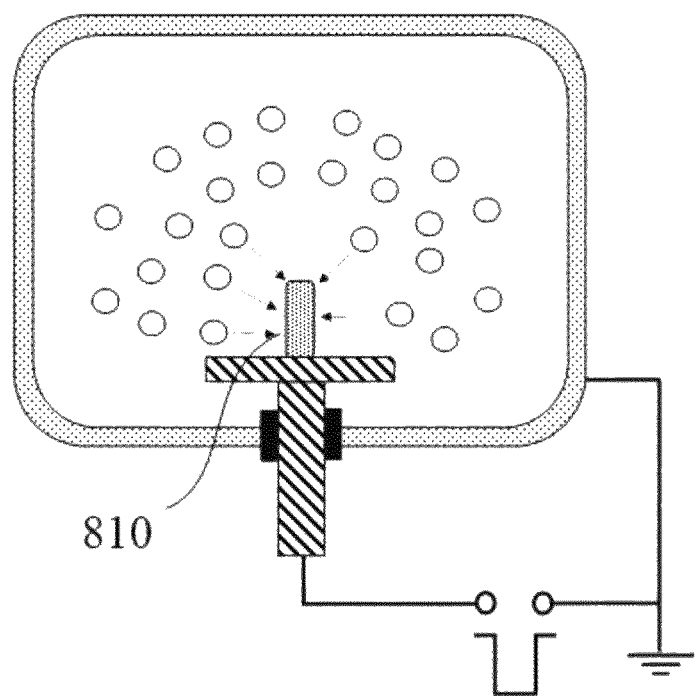
FIG. 8 depicts a schematic diagram showing a method of preparing a composition by using a plasma immersion ion implantation.

Please refer to FIG. 8, which depicts a schematic diagram showing a method of preparing a composition by using a plasma immersion ion implantation 800. In this embodiment, the plasma immersion ion implantation 800 is used for embedding neutron capture elements into nanodiamond particles which are located on a bombardment target 810 of the plasma immersion ion implantation 800.

In summary, in the present invention, the composition comprises neutron capture elements embedded into nanodiamond particles by using ion implantation for treating tumor cells through NCT. The amount of neutron capture elements embedded into each nanodiamond particle can be controlled through ion implantation dose to result a higher amount of neutron capture elements in the composition than the conventional NCT drug. The uptake of neutron capture elements containing in the composition by the tumor cells according to the present invention can be significantly increased, thereby achieving the delivery of a high concentration of neutron capture elements to the tumor cells while keeping the concentration of the neutron capture elements relatively low in the surrounding normal cells. Furthermore, the composition is prepared by synthesizing nanodiamond particles embedded with neutron capture elements with a targeting drug agent and such nanodiamond therapeutic agent is delivered to tumor cells for NCT, thereby enhancing NCT effect.

The above descriptions are merely preferable embodiments of the present invention, but are not intended to limit the scope of the present invention. Any modification or replacement made by those skilled in the art without departing from the spirit and principle of the present invention should fall within the protection scope of the present invention. Therefore, the protection scope of the present invention is subject to the appended claims.

What is claimed is:

1. A composition capable of being delivered to tumor cells in vivo for neutron capture therapy, comprising: a plurality of complexes, wherein each complex consists of a nanodiamond particle and at least one boron-10 particle, wherein the complex is composed of embedding the at least one boron-10 particle into the nanodiamond particle by using an ion implantation system, and wherein nanodiamond particles of the plurality of complexes are arranged loosely and individually.

2. The composition for neutron capture therapy as claimed in claim 1, wherein the ion implantation system used to embed boron-10 into the nanodiamond particle comprises:
   an ion source assembly, for generating ions;
   an extraction assembly, for extracting the ions from the ion source assembly to form an ion beam;
   an analyzing magnet, for selecting the at least one boron-10 particle from the ion beam; and
   an end station, for supporting a workpiece which holds the nanodiamond particle and located in a path of the ion beam such that the at least one boron-10 particle is implanted into the workpiece thereby to embed the at least one boron-10 particle into the nanodiamond particle.

3. The composition for neutron capture therapy as claimed in claim 1, wherein the ion implantation system used to embed boron-10 into the nanodiamond particle comprises a plasma immersion ion implantation system.

4. The composition for neutron capture therapy as claimed in claim 1, further comprising at least one chemotherapeutic drug, wherein the at least one chemotherapeutic drug is conjugated with the complex.

5. The composition for neutron capture therapy as claimed in claim 4, wherein the at least one chemotherapeutic drug is selected from the group consisting of doxorubicin and daunorubicin.

6. The composition for neutron capture therapy as claimed in claim 1, further comprising at least one neutron capture therapy drug coupled with the complex for targeted delivery of the composition to tumor cells.

7. The composition for neutron capture therapy as claimed in claim 6, wherein the at least one neutron capture therapy drug is selected from the group consisting of BPA, BSH, and BSH-3R.

8. The composition for neutron capture therapy as claimed in claim 1, further comprising at least one drug delivery agent connected with the complex to deliver the nanodiamond particle embedded with the at least one boron-10 particle of the complex to tumor cells for performing neutron capture therapy.

9. A composition capable of being delivered to tumor cells in vivo for neutron capture therapy, comprising:
    a plurality of complexes, wherein each complex consists of a nanodiamond particle and at least one boron-10 particle, wherein the complex is composed of embedding the at least one boron-10 particle into the nanodiamond particle, and wherein nanodiamond particles of the plurality of complexes are arranged loosely and individually; and
    an agent for facilitating the treatment of tumor cells being connected with the complex.

10. The composition for neutron capture therapy as claimed in claim 9, wherein the agent is chemotherapeutic drug.

11. The composition for neutron capture therapy as claimed in claim 10, wherein the chemotherapeutic drug is selected from the group consisting of doxorubicin and daunorubicin.

12. The composition for neutron capture therapy as claimed in claim 9, wherein the agent is neutron capture therapy drug for targeted delivery of the composition to the tumor cells.

13. The composition for neutron capture therapy as claimed in claim 12, wherein the neutron capture therapy drug is selected from the group consisting of BPA, BSH, and BSH-3R.

14. The composition for neutron capture therapy as claimed in claim 9, wherein the agent is a drug delivery agent to deliver the complex to the tumor cells for performing neutron capture therapy.

* * * * *